United States Patent [19]

Hahn et al.

[11] Patent Number: 5,256,826
[45] Date of Patent: Oct. 26, 1993

[54] PREPARATION OF AROMATIC CARBONYL OR SULFONYL COMPOUNDS WITH AN ARYL ETHER STRUCTURE

[75] Inventors: Erwin Hahn, Heidelberg; Heinrich J. Eilingsfeld, Frankenthal; Helmut Reichelt; Alexander Aumueller, both of Neustadt; Bernd Hupfeld, Speyer, all of Fed. Rep. of Germany

[73] Assignee: BASF Aktiengesellschaft, Ludwigshafen, Fed. Rep. of Germany

[21] Appl. No.: 937,416

[22] Filed: Aug. 31, 1992

[30] Foreign Application Priority Data

Sep. 19, 1991 [DE] Fed. Rep. of Germany ....... 4131144

[51] Int. Cl.$^5$ .................. C07C 315/04; C07C 45/61; C07C 67/24
[52] U.S. Cl. ...................................... 568/33; 568/315; 568/316; 568/433; 560/64; 560/60; 560/61
[58] Field of Search ................. 568/315, 33, 636, 635, 568/316, 433; 560/64, 60, 61

[56] References Cited

U.S. PATENT DOCUMENTS 4,577,034 3/1986 Durvasula .

FOREIGN PATENT DOCUMENTS 262919 4/1988 European Pat. Off. .
0282096 9/1988 European Pat. Off. .
0384043 8/1990 European Pat. Off. .

*Primary Examiner*—Marianne M. Cintins
*Assistant Examiner*—Margaret J. Page
*Attorney, Agent, or Firm*—Oblon, Spivak, McClelland, Maier & Neustadt

[57] ABSTRACT

A process for the preparation of aromatic carbonyl or sulfonyl compounds with a diaryl ether structure by reacting phenols with halogenated carbonyl- or sulfonylaromatic compounds in a dipolar aprotic solvent is carried out in the presence of catalytic amounts of alkali metal nitrite or an aromatic nitro, nitroso, azo, azoxy or hydrazo compound.

6 Claims, No Drawings

PREPARATION OF AROMATIC CARBONYL OR SULFONYL COMPOUNDS WITH AN ARYL ETHER STRUCTURE

The present invention relates a novel process for preparing aromatic carbonyl or sulfonyl compounds with an aryl ether structure by reacting phenols with halogenated carbonyl- or sulfonylaromatic compounds in a dipolar aprotic solvent.

Aromatic carbonyl or sulfonyl compounds with an aryl ether structure (e.g. 4,4'-diphenoxybenzophenone) are required for preparing polymers resistant to high temperatures, e.g. polyether ketones. They are used in highly pure form for this purpose.

For example, EP-A 262 919 discloses the preparation of such compounds by reacting diphenyl ether with halobenzoyl halides. The disadvantages of this process are the formation of by-products (oligomers) and the fact that phosgene must be used to prepare the halobenzoyl halides.

Furthermore, EP-A 282 096 describes a preparation in which hydroxyaryl compounds are reacted with haloaromatic compounds. The disadvantage of this procedure is the low reactivity of chloroaromatic compounds. The consequence of this is that it is necessary to use fluoroaromatic compounds which are much more costly than chloroaromatic compounds.

It is an object of the present invention to provide a novel process for preparing aromatic carbonyl or sulfonyl compounds with an aryl ether structure which can be carried out in a straightforward manner. The intention was that hydroxyaryl compounds be reacted in the novel process with chloro- or bromo-aromatic compounds of low reactivity to give the required products in high yield and purity.

We have found that this object is achieved by preparing aryl ethers of the formula I

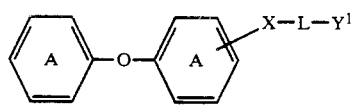

(I)

where the ring A is unsubstituted or substituted and can be benzo-fused,
X is carbonyl or sulfonyl,
L is a chemical bond or a linker and
Y¹ a) in the case where L is a linker, is halogen or the radical of the formula

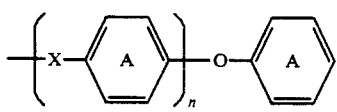

where n is 0 or 1 and X and the ring A each have the abovementioned meanings,
b) in the case where L is a chemical bond and X is carbonyl, is hydrogen, $C_1$–$C_4$-alkyl, $C_1$–$C_4$-alkoxy or the radical of the formula

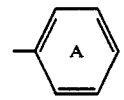

where the ring A has the abovementioned meanings, or
c) in the case where L is a chemical bond and X is sulfonyl, is the radical of the formula

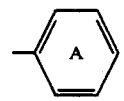

where the ring A has the abovementioned meanings, by reaction of phenols of the formula II

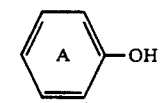

(II)

where the ring A has the abovementioned meanings, with halogen compounds of the formula III

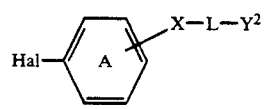

(III)

where
Hal is chlorine or bromine and
Y² is a radical of the formula

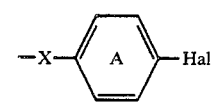

where X, Hal and the ring A each have the abovementioned meanings, or are the abovementioned radical Y¹, and X, Hal and the ring A each have the abovementioned meanings, in a dipolar aprotic solvent in the presence of a base, when the reaction is carried out at from 60° to 240° C. in the presence of a catalytic amount of a compound selected from the class composed of alkali metal nitrite and compounds of the formula IV

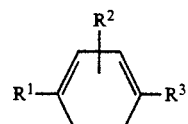

(IV)

where
R¹ and R² are identical or different and each, independently of the other, is hydrogen, $C_1$–$C_{12}$-alkyl which is unsubstituted or substituted by phenyl, or is $C_1$–$C_{12}$-alkoxy, halogen or nitro and
R³ is nitro, nitroso or a radical of the formula

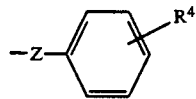

where

R[4] is hydrogen, $C_1$-$C_4$-alkyl or halogen and Z is a radical of the formula —N=N,

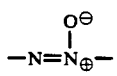

pr —NH—NH—, with the proviso that when R[3] is nitro at least one of the two radicals R[1] and R[2] is halogen.

All alkyl groups in the formula I, II or III can be both straight-chain and branched.

Suitable substituents for substituted phenyl or naphthyl in the formula I, II or III are, for example, $C_1$-$C_4$-alkyl, hydroxyl, $C_1$-$C_4$-alkoxy, phenyl or phenyl substituted by $C_1$-$C_4$-alkyl or $C_1$-$C_4$-alkoxy. The rings can, as a rule, be mono- to trisubstituted.

When Y[1] is halogen, suitable examples are fluorine or, in particular, chlorine or bromine.

When L is a linker, suitable examples are phenylene, biphenylylene, naphthylene or a radical of the formula

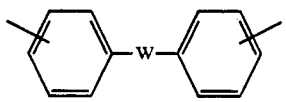

where W is oxygen, sulfur, carbonyl or sulfonyl.

Examples of R[1], R[2] and R[4] are methyl, ethyl, propyl, isopropyl, butyl, isobutyl, sec-butyl, fluorine, chlorine or bromine.

Further examples of R[1] and R[2] are pentyl, isopentyl, neopentyl, tert-pentyl, hexyl, 2-methylpentyl, heptyl, 1-ethylpentyl, octyl, 2-ethylhexyl, isooctyl, nonyl, isononyl, decyl, isodecyl, undecyl, dodecyl, (the names isooctyl, isononyl and isodecyl are trivial names derived from the alcohols obtained in the oxo synthesis, cf. Ullmanns Encyklopädie der technischen Chemie, 4th edition, Volume 7, pages 215 to 217, and Volume 11, pages 435 and 436), benzyl, 1- or 2-phenylethyl, methoxy, ethoxy, propoxy, isopropoxy, butoxy, isobutoxy, secbutoxy, pentyloxy, isopentyloxy, neopentyloxy, tert-pentyloxy, hexyloxy, 2-methylpentyloxy, heptyloxy, 1-ethylpentyloxy, octyloxy, 2-ethylhexyloxy, isooctyloxy, nonyloxy, decyloxy, isodecyloxy, undecyloxy or dodecyloxy.

Examples of suitable dipolar aprotic solvents which can be used in the process according to the invention are acetone, acetonitrile, nitromethane, N,N-di-methylformamide, N,N-dimethylacetamide, N-methyl-pyrrolidinone, tetramethylurea, hexamethylphosphoric triamide, dimethyl sulfoxide, tetrahydrothiophene 1,1-dioxide (sulfolane), diethers of ethylene glycol such as ethylene glycol dimethyl or diethyl ether, or ethylene carbonate.

Examples of suitable bases which can be used in the process according to the invention are alkali metal carbonates such as sodium or potassium carbonate, or mixtures thereof.

If the process according to the invention is carried out in the presence of an alkali metal nitrite, suitable examples are sodium and potassium nitrites.

Particular emphasis is placed on a procedure for preparing aryl ethers of the formula I where the ring A is unsubstituted, is substituted by phenyl or is benzo-fused.

Particular emphasis is furthermore placed on a procedure for preparing aryl ethers of the formula I where L is a linker.

Particular emphasis is furthermore placed on a procedure for preparing aryl ethers of the formula I where phenols of the formula II are reacted with halogen compounds of the formula III where Hal is chlorine.

Of particular interest is a procedure for preparing aryl ethers of the formula I where L is phenylene, especially 1,4-phenylene, or biphenylylene, especially 4,4'-biphenylylene.

A procedure for preparing aryl ethers of the formula Ia

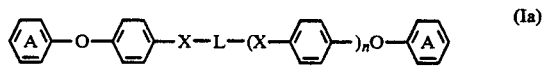

where the ring A is unsubstituted, substituted by phenyl or is benzo-fused,

X is carbonyl or sulfonyl
L is phenylene or biphenylene and
n is 0 or 1, by reacting phenols of the formula II

where the ring A has the last-mentioned meaning, with halogen compounds of the formula IIIa

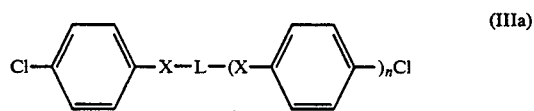

where X, L and n each have the abovementioned meaning, is preferred.

A procedure for preparing aryl ethers of the formula Ib

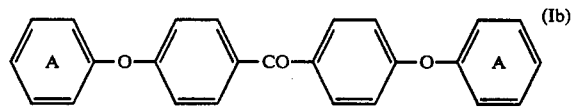

where the ring A is unsubstituted, is substituted by phenyl or is benzo-fused, by reacting phenols of the formula II

where the ring A has the last-mentioned meaning, with 4,4'-dichlorobenzophenone, is particularly preferred.

Particular emphasis is furthermore placed on a procedure for preparing aryl ethers of the formula Ic

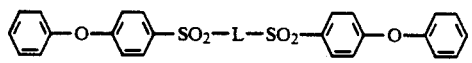

where L is phenylene or naphthylene, by reacting phenol with halogen compounds of the formula IIIb

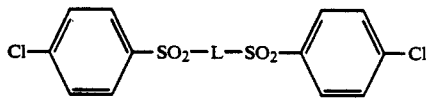

where L has the last-mentioned meaning.

An important procedure is one in which the reaction is carried out in the presence of a compound of the formula IV.

A particularly important procedure is one in which the reaction is carried out in the presence of a compound of the formula IV where $R^1$ is hydrogen, $R^2$ is hydrogen or halogen and $R^3$ is nitro or a radical of the formula

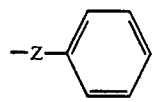

where Z has the abovementioned meanings.

Compounds of the formula IV which should be particularly mentioned are 1-chloro-2-nitrobenzene, 1-chloro-3-nitrobenzene, azobenzene, azoxybenzene or hydrazobenzene.

Particularly suitable dipolar aprotic solvents in the process according to the invention are N,N-dimethylformamide or, in particular, N-methylpyrrolidinone.

Potassium carbonate is particularly suitable as base in the process according to the invention.

The novel process is carried out at from 60° to 240° C., preferably from 80° to 200° C., and normally under atmospheric pressure.

The phenol II:halogen compound III (as monohalogen compound) molar ratio is, as a rule, 2:1, preferably 1.05:1. When the compound III is a dihalogen compound, the abovementioned molar ratio is, as a rule, 4:1, preferably 2.1:1.

The base:phenol II molar ratio is, as a rule, from 1.5:1 to 1:1, preferably about 1:1.

The compound IV is used in catalytic amounts, which means within the scope of the invention from 0.1 to 20 mol %, preferably from 1 to 10 mol %, in each case based on the halogen compound III. It is possible to increase this amount, but this has no advantages.

The amount of dipolar aprotic solvent in the novel process is, as a rule, from 200 to 1000% of the weight of phenol II.

The process according to the invention can be carried out both continuously and batchwise. It is expediently carried out in such a way that solvent, phenol II, halogen compound III, base and alkali metal nitrite or compound IV are mixed and heated, with stirring and possibly under a protective gas atmosphere (e.g. nitrogen or helium), to the abovementioned temperature. The mixture is then stirred at this temperature for, in general from 4 to 10 hours.

The reaction mixture is worked up by cooling to about 10°-70° C. and then introducing into water. This results in the aryl ether I precipitating, and it can be, for example, removed by filtration, washed with water and dried.

One advantage of the novel process is that it can be carried out in an industrially straightforward manner, and it is possible to use unreactive chlorine or bromine compounds. The aryl ethers of the formula I are obtained in good yield and high purity. This is particularly important because, as mentioned above, the target compounds are used as intermediates for preparing polymers which are resistant to high temperatures and, for this purpose, must be in highly pure form.

The Examples illustrate the invention.

EXAMPLE 1

Preparation of 4,4'-diphenoxybenzophenone (comparative)

110 ml of N-methylpyrrolidinone (NMP), 24.2 g (0.257 mol) of phenol, 31.38 g (0.125 mol) of 4,4'-dichlorobenzophenone and 35.5 g (0.257 mol) of potassium carbonate were introduced under a nitrogen atmosphere at room temperature into a 500 ml flask with distillation head, stirrer and reflux condenser, and the mixture was then heated to 190°-195° C. About 5 to 6 ml of water/NMP mixture were distilled out at 185°-190° C. The progress of the reaction was followed by thin-layer chromatography. After 10 hours at 190° C., no further reaction was detected (no precursor present in TLC). The reaction solution was cooled to about 80° C. and introduced into 350 ml of water with vigorous stirring. The precipitated product was filtered off, washed with 1000 ml of water and dried under reduced pressure. HPLC analysis of a sample showed 76.5% of 4,4'-diphenoxybenzophenone, 19.2% of 4-chloro-4'-phenoxybenzophenone and 4.3% of unidentified impurities.

EXAMPLES 2 to 7 (According to the Invention)

The reaction was carried out as in Example 1 but in the presence of the catalysts listed in the following Table 1.

TABLE 1

| Example No. | Catalyst | Reaction time [h] | Yield [%] | Purity [HPLC] [%] |
| --- | --- | --- | --- | --- |
| 2 | 1-Chloro-2-nitrobenzene (1 g) | 6 | 98.5 | 99.7 |
| 3 | 1-Chloro-3-nitrobenzene (2 g) | 6 | 97.9 | 98.9 |
| 4 | Azobenzene (2 g) | 6 | 98.3 | 99.4 |
| 5 | Hydrazobenzene (2 g) | 6 | 97.8 | 98.3 |
| 6 | Azoxybenzene (2 g) | 6 | 98.7 | 99.5 |
| 7 | Potassium nitrite (5 g) | 6 | 98.8 | 99.2 |

EXAMPLE 8

Preparation of 4,4'-bis(1-naphthyloxy)benzophenone (Comparative)

The reaction was carried out as in Example 1 using 120 ml of NMP, 31.38 g (0.125 mol) of 4,4'-dichlorobenzophenone, 37.0 g (0.257 mol) of 1-naphthol and 35.5 g (0.257 mol) of potassium carbonate. After reaction for 10 hours, no further progress was observed, and the mixture was worked up. HPLC analysis of a sample showed 69.4% of 4,4'-bis(1-naphthyloxy)benzophenone, 27.2% of 4-(1-naphthyloxy)-4'-chlorobenzophenone and 3.4% of unidentified by-products.

EXAMPLES 9 to 14 (According to the Invention)

The reaction was carried out as in Example 8, but in the presence of the catalysts listed in the following Table 2.

TABLE 2

| Example No. | Catalyst | Reaction time [h] | Yield [%] | Purity [HPLC] [%] |
|---|---|---|---|---|
| 9 | 1-Chloro-2-nitrobenzene (1 g) | 8 | 97.3 | 98.8 |
| 10 | 1-Chloro-3-nitrobenzene (2 g) | 8 | 96.6 | 98.3 |
| 11 | Azobenzene (2 g) | 8 | 96.3 | 97.9 |
| 12 | Hydrazobenzene (2 g) | 8 | 96.6 | 97.9 |
| 13 | Azoxybenzene (2 g) | 8 | 98.1 | 98.9 |
| 14 | Potassium nitrite (5 g) | 8 | 98.1 | 98.9 |

EXAMPLE 15

Preparation of 4,4'-bis(4-biphenyloxy)benzophenone (Comparative)

The reaction was carried out as in Example 1 using 250 ml of NMP, 31.4 g (0.125 mol) of 4,4'-dichlorobenzophenone, 42.5 g of 4-hydroxybiphenyl and 26.0 g (0.26 mol) of potassium carbonate. After reaction for 10 hours, no further progress was detected, and the mixture was worked up. HPLC analysis of a sample showed 71.4% of 4,4'-bis(4-biphenyloxy)benzophenone, 25.8% of 4-(4-biphenyloxy)-4'-chlorobenzophenone and 2.8% of unidentified by-products.

EXAMPLES 16 to 21 (According to the Invention)

The reaction was carried out as in Example 15 but in the presence of the catalysts listed in the following Table 3.

TABLE 3

| Example No. | Catalyst | Reaction time [h] | Yield [%] | Purity [HPLC] [%] |
|---|---|---|---|---|
| 16 | 1-Chloro-2-nitrobenzene (1 g) | 8 | 98.7 | 98.9 |
| 17 | 1-Chloro-3-nitrobenzene (2 g) | 8 | 98.2 | 98.1 |
| 18 | Azobenzene (2 g) | 8 | 97.3 | 97.9 |
| 19 | Hydrazobenzene (2 g) | 8 | 96.9 | 97.4 |
| 20 | Azoxybenzene (2 g) | 8 | 98.7 | 98.8 |
| 21 | Potassium nitrite (5 g) | 8 | 98.5 | 98.9 |

EXAMPLE 22

Preparation of 4,4'-bis(4-phenoxyphenylsulfonyl)biphenyl (Comparative)

The reaction was carried out as in Example 1 using 62.9 g (0.125 mol) of 4,4'-bis(4-chlorphenylsulfonyl)biphenyl, 23.5 g (0.25 mol) of phenol, 36.0 g (0.26 mol) of potassium carbonate and 250 ml of NMP. After reaction for 8 hours, no further progress was detected, and the mixture was worked up. HPLC analysis of a sample showed 70.3% of 4,4'-bis(4-phenoxyphenylsulfonyl)biphenyl, 27.8% of 4-(4-phenoxyphenylsulfonyl)-4'-chlorophenylsulfonylbiphenyl and 1.9% of unidentified by-products.

EXAMPLES 23 to 28 (According to the Invention)

The reaction was carried out as in Example 22 but in the presence of the catalysts listed in the following Table 4.

TABLE 4

| Example No. | Catalyst | Reaction time [h] | Yield [%] | Purity [HPLC] [%] |
|---|---|---|---|---|
| 23 | 1-Chloro-2-nitrobenzene (1 g) | 5 | 97.9 | 97.7 |
| 24 | 1-Chloro-3-nitrobenzene (2 g) | 5 | 97.5 | 97.5 |
| 25 | Azobenzene (2 g) | 5 | 97.0 | 96.9 |
| 26 | Hydrazobenzene (2 g) | 5 | 98.0 | 97.2 |
| 27 | Azoxybenzene (2 g) | 5 | 98.7 | 98.5 |
| 28 | Potassium nitrite (5 g) | 5 | 98.3 | 98.4 |

We claim:

1. A process for preparing an aryl ether of the formula I

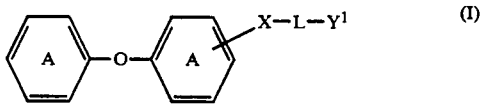

wherein
the ring A is unsubstituted, substituted or benzofused;
X is carbonyl or sulfonyl;
L is a chemical bond or a linking group; and
i) when L is a linking group, $Y^1$ is halogen or a radical of the formula

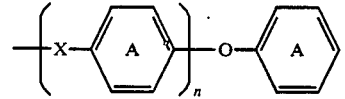

where n is 0 or 1 and X and the ring A have the abovementioned meanings;
ii) when L is a chemical bond and X is carbonyl, $Y^1$ is hydrogen, $C_1$–$C_4$-alkyl, $C_1$–$C_4$-alkoxy or a radical of the formula

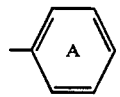

where the ring A has the above-mentioned meansings; or
iii) when L is a chemical bond and X is sulfonyl, $Y^1$ is a radical of the formula

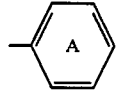

where the ring A has the above-mentioned meanings,, comprising:
reacting a phenol of the formula II

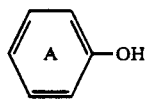  (II)

where the ring A has the above-mentioned meanings, with a halogen compound of the formula III

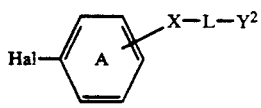  (III)

wherein
Hal is chlorine or bromine;
L is a chemical bond or a linking group; and
$Y^2$ is a radical of the formula

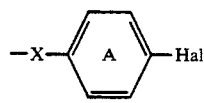

wherein when L is a linking group, $Y^2$ is a radical of the formula

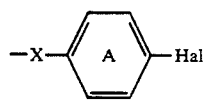

or the above-mentioned radical $Y^1$,
wherein
i) when L is a linking group, $Y^1$ is halogen or a radical of the formula

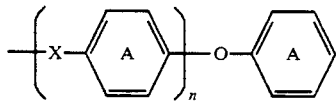

where n is 0 or 1 and X and the ring A have the above-mentioned meansings;
ii) when L is a chemical bond and X is carbonyl, $Y^1$ is hydrogen, $C_1$-$C_4$-alkyl, $C_1$-$C_4$-alkoxy or a radical of the formula

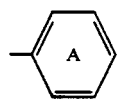

where the ring A has the above-mentioned meanings; or
iii) when L is a chemical bond and X is sulfonyl, $Y^1$ is a radical of the formula

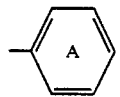

where the ring A has the above-mentioned meanings, where X, Hal and the ring A each have the above-mentioned meanings,
in a dipolar aprotic solvent in the presence of a base, at a reaction temperature of from 60° to 240° C., in the presence of a catalytically effective amount of a compound selected from the group consisting of an alkali metal nitrite compound, a compound of the formula IV

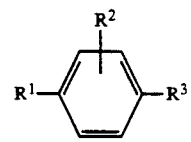  (IV)

and a mixture thereof; wherein
$R^1$ and $R^2$ are identical or different and each independently is hydrogen, $C_1$-$C_{12}$-alkyl which is unsubstituted or substituted by phenyl, or is $C_1$-$C_{12}$-alkoxy, halogen or nitro, and
$R^3$ is nitro, nitroso, or a radical of the formula

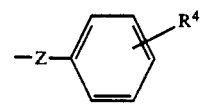

where $R^4$ is hydrogen, $C_1$-$C_4$-alkyl or halogen and Z is a radical of the formula —N=N,

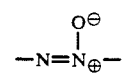

or —NH—NH—, with the proviso that when $R^3$ is nitro, at least one of the two radicals $R^1$ and $R^2$ is halogen.

2. A process as claimed in claim 1, wherein the ring A is unsubstituted, is substituted by phenyl or is benzo-fused.

3. A process as claimed in claim 1, wherein L is a linking group.

4. A process as claimed in claim 1, wherein Hal is chlorine.

5. A process as claimed in claim 1, wherein aryl ethers of the formula Ia

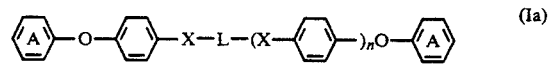  (Ia)

where
the ring A is unsubstituted, is substituted by phenyl or is benzo-fused,
X is carbonyl or sulfonyl,
L is phenylene or biphenylylene and
n is 0 or 1, are prepared by reacting phenols of the formula II

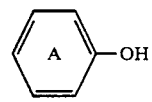  (II)

where the ring A has the abovementioned meanings,
with halogen compounds of the formula IIIa
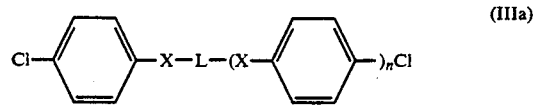
where X, L and n each have the abovementioned meanings.
6. A process as claimed in claim 1, wherein the reaction is carried out in the presence of a compound of the formula IV.
* * * * *